United States Patent [19]

Drake

[11] Patent Number: 4,618,722

[45] Date of Patent: Oct. 21, 1986

[54] PREPARATION OF ORGANIC SULFIDES

[75] Inventor: Charles A. Drake, Bartlesville, Okla.

[73] Assignee: Phillips Petroleum Company, Bartlesville, Okla.

[21] Appl. No.: 742,677

[22] Filed: Jun. 10, 1985

Related U.S. Application Data

[63] Continuation-in-part of Ser. No. 701,705, Feb. 14, 1985, abandoned.

[51] Int. Cl.$^4$ ........................................... C07C 149/10
[52] U.S. Cl. ...................................... 568/59; 568/38; 568/58; 568/60
[58] Field of Search ........................ 568/38, 58, 59, 60

[56] References Cited

U.S. PATENT DOCUMENTS

| | | | |
|---|---|---|---|
| 2,908,716 | 10/1959 | Cisney et al. | 568/60 |
| 3,387,039 | 6/1968 | Doss | 568/26 |
| 3,799,999 | 3/1976 | Gordon et al. | 570/260 |
| 4,072,718 | 2/1978 | Billings | 568/21 |

FOREIGN PATENT DOCUMENTS 0048104  4/1981  U.S.S.R. ................................ 568/59

OTHER PUBLICATIONS

C. Lenca et al, Synthesis (1981), (2), 141–142, The Reduction of Sulfoxides with Tert-butyl Bromide.
F. Seiichi et al, Chem. Abst., vol. 72:59472v (1970), Amine-Type Corrosion Inhibitors.

*Primary Examiner*—Donald G. Daus
*Assistant Examiner*—Mary E. Ceperley
*Attorney, Agent, or Firm*—K. K. Brandes

[57] ABSTRACT

A process for preparing dihydrocarbyl sulfides comprises the step of simultaneously contacting (a) a dialkyl sulfoxide, preferably dimethyl sulfoxide, with (b) a hydrocarbyl halide, particularly an alkyl or alkenyl bromide, and (c) a metal carboxylate, preferably an alkali metal acetate, under such conditions as will produce at least one alkyl hydrocarbyl sulfide or alkenyl hydrocarbyl sulfide.

20 Claims, No Drawings

PREPARATION OF ORGANIC SULFIDES

This is a continuation-in-part application of my copending application having Ser. No. 701,705, now abandoned, filed Feb. 14, 1985.

BACKGROUND OF THE INVENTION

This invention relates to a process for preparing organic sulfides. In another aspect, this invention relates to a process for preparing unsymmetrical dihydrocarbyl sulfides. In still another aspect, this invention relates to the preparation of methyl alkyl sulfides and methyl alkenyl sulfides. In a further aspect, this invention relates to a process for the catalytic production of organic sulfides.

Processes for preparing organic sulfides such as symmetrical and unsymmetrical dialkyl sulfides and alkyl alkenyl sulfides, which are useful as solvents, surfactants and intermediates in organic syntheses, are known. One such prior art process is the reaction of an olefin and a mercaptan in the presence of a free radical initiator as catalyst. However, there is an ever present need to develop new processes for preparing sulfides, especially processes utilizing simpler catalyst systems and simpler reaction conditions than those previously known.

SUMMARY OF THE INVENTION

It is an object of this invention to prepare organic sulfides. It is another object of this invention to prepare symmetrical and unsymmetrical dihydrocarbyl sulfides. It is another object of this invention to prepare symmetrical and unsymmetrical dialkyl sulfides, alkyl alkenyl sulfides and alkyl cycloalkyl sulfides. It is a further object of this invention to prepare unsymmetrical methyl alkyl sulfides. It is still another object of this invention to prepare methyl alkenyl sulfides. It is a still further objective to prepare methyl cycloalkyl sulfides. It is an additional object of this invention to prepare organic sulfides in the presence of a catalyst.

In accordance with this invention, dihydrocarbyl sulfides, suitable as solvents or surfactants or intermediates in organic syntheses, are prepared by contacting a hydrocarbyl halide with a dialkyl sulfoxide and a metal carboxylate. The reaction is carried out under such conditions as to yield at least one sulfide as a reaction product.

In one embodiment, an alkyl halide or an alkenyl halide is contacted with a dialkyl sulfoxide in the presence of a Group IA metal carboxylate under reaction conditions such as to prepare dialkyl sulfides or alkyl alkenyl sulfides. In a preferred embodiment, an alkyl bromide or alkenyl bromide is contacted with dimethyl sulfoxide in the presence of a Group IA metal acetate at an elevated temperature. In the presently more preferred embodiment, the alkyl bromide or alkenyl bromide contains 10–20 C-atoms per molecule, and the metal acetate is potassium acetate.

DETAILED DESCRIPTION OF THE INVENTION

A process for preparing dihydrocarbyl sulfides of the general formula R-S-R' is provided, wherein R is an alkyl group containing from 1 to 8 carbon atoms and R' is selected from the group consisting of alkyl groups containing from 1 to 25 carbon atoms, alkenyl groups containing from 3 to 25 carbon atoms and cycloalkyl groups containing from 5 to 25 carbon atoms, with the understanding that the alkyl and alkenyl groups can be cycloalkyl substituted, and the cycloalkyl groups can be alkyl substituted. In yet other words, R' can be defined as a non-aromatic hydrocarbon radical having up to 25 carbon atoms and 0 or 1 carbon-carbon double bond.

Examples of the R group are methyl, ethyl, propyl, n-butyl, sec-butyl, n-pentyl, n-hexyl, 2-methylpentyl, n-octyl and the like. Preferably R is the methyl group. Non-limiting examples of R' are methyl, ethyl, propyl groups, butyl groups, hexyl groups, octyl groups, decyl groups, dodecyl groups, hexadecyl groups, octadecyl groups, eicosyl groups, pentacosyl groups, propenyl, butenyl groups, hexenyl groups, decenyl groups, hexadecenyl groups, eicosenyl groups, pentacosenyl groups, cyclopentyl, cyclohexyl, methylcyclohexyl groups, ethylcycloheptyl groups, dimethylcycloheptyl groups, dimethylcyclooctyl groups, diethylcyclooctyl groups, tributylcyclooctyl groups and the like. Preferably R' is an alkyl or alkenyl group having from 3–20, more preferably 10–20, carbon atoms, presently most preferably the 11-hexadecenyl group.

The process for preparing dihydrocarbyl sulfides in accordance with this invention comprises the step of simultaneously contacting:

(a) a dialkyl sulfoxide of the formula

wherein the radicals R, which can be the same or different, are defined as above; and (b) a hydrocarbyl halide of the formula R'X; wherein R' is defined as above, and X is selected from the group consisting of Cl, Br, and I; and (c) a metal carboxylate of the formula

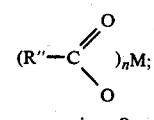

a wherein R'' is H or an alkyl group having from 1–4 carbon atoms; n is 1 or 2; and M is a mono- or divalent cation of a metal selected from the group of metals of Groups IA, IIA, IVA, IB, IIB, VIIB and VIII of the Periodic Table (as defined in College Chemistry by W. H. Nebergall et al, D. C. Heath and Co., 1972); under such conditions as will result in a reaction product comprising at least one alkylhydrocarbyl sulfide of the formula R-S-R'. M is preferably a Group IA metal (alkali metal).

Non-limiting examples of

are dimethyl sulfoxide, diethyl sulfoxide, methyl ethyl sulfoxide, dipropyl sulfoxide, diisopropyl sulfoxide, di-n-pentyl sulfoxide, di-n-hexyl sulfoxide, di-(2-methylpentyl) sulfoxide, didoctyl sulfoxide, methyl octyl sulfoxide, ethyl octyl sulfoxide, and the like. The preferred dialkyl sulfoxide is dimethyl sulfoxide.

Non-limiting examples of R'-X are methyl chloride, methyl bromide, methyl iodide, ethyl chloride, ethyl bromide, ethyl iodide, propyl bromides, butyl chlorides, butyl bromides, pentyl bromides, pentyl bromides, octyl bromides, decyl iodides, hexadecyl chlorides, hexadecyl bromides, eicosyl bromides, eicosyl iodides, pentacosyl chlorides, pentacosyl bromides, pentacosyl iodides, propenyl bromides, butenyl chlorides, butenyl iodides, pentenyl bromides, hexenyl iodides, octenyl chlorides, decenyl bromides, hexadecenyl chlorides, hexadecenyl bromides, hexadecenyl iodides, eicosenyl bromides, pentacosenyl chlorides, pentacosenyl bromides, pentacosenyl iodides, cyclopentyl bromides, cyclohexyl chloride, cyclohexyl iodide, methylcyclohexyl bromides, ethylcycloheptyl bromides, dimethylcyclooctyl chlorides, didethylcyclooctyl iodides, tributylcyclooctyl bromides, and the like. Presently preferred is 11-hexadecenyl bromide.

Non-limiting examples of

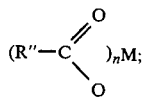

are sodium formate, sodium acetate, potassium acetate, lithium acetate, calcium acetate, nickel acetate, zinc acetate, sodium propionate, magnesium propionate, sodium butyrate, cesium butyrate, barium butyrate, iron(II) butyrate and the like. The presently preferred metal carboxylate is potassium acetate.

The three process ingredients (a), (b) and (c) can be contacted in any suitable manner, optionally in the presence of at least one inert solvent such as paraffins or cycloparaffins that are normally liquid, i.e., liquid at room temperature (about 25° C.) and about 1 atm pressure, preferably n-hexane. The process ingredients can be added to a suitable reaction vessel essentially simultaneously or sequentially in any order. Or two ingredients, e.g., (a) and (b) can be premixed, e.g., in a vessel with agitating means or with static mixing means, and then (c) can be added to the mixture. The process can be a batch process or a continuous process. In both types of processes, intimate simultaneous contacting of the process ingredients (a), (b) and (c) is achieved by any mixing/agitating means known to those skilled in art of organic syntheses.

Any suitable mole ratio of process ingredients (a), (b) and (c) can be employed in the process of this invention. Generally an excess of at least one of the process ingredients, usually the less expensive one(s), is used. The relative amounts of process ingredients (a), (b) and (c) are not considered critical since unreacted ingredients can be recycled to the reactor. The relative amounts can be determined for any specific species of (a), (b) and (c) and for specific reaction conditions so as to attain maximum conversion of the most expensive ingredient at an optimal rate of reaction. The presently preferred mole ratio of (a):(b) ranges from about 1:1to about 400:1, more preferably from about 15:1 to about 30:1. The presently preferred mole ratio of (a):(c) ranges from about 2:1 to about 40:1, more preferably from about 6:1 to about 15:1. The presently preferred mole ratio of (b):(c) ranges from about 1:10 to about 2:1, more preferably from about 1:5 to about 1:1.

Heating of ingredients (a), (b) and (c) is generally required to accomplish a reaction. Any suitable temperature that will cause and maintain a controllable reaction can be employed. Any feasible heating means can be utilized. It is within the scope of this invention to preheat one or more of the process ingredients before they are introduced into a reactor, which is heated to maintain a suitable temperature. Generally the reaction temperature ranges from about 50° C. to about 250° C., more preferably from about 100° C. to about 150° C.

The reaction pressure can vary from subatmospheric pressure to elevated pressure such as up to 500 psig. The selection of the reaction pressure will greatly depend on the reaction temperature, the volatility of process ingredients and products, and the specific reactor design. Generally the pressure is approximately atmospheric (about 1 atm, 0 psig).

The reaction time, i.e., the time of intimate, simultaneous contact of process ingredients (a), (b) and (c), can vary from 1 minute to about 50 hours and will preferably be in the range of about 0.2 to about 2 hours. The actual reaction time will greatly depend on the flow rates of process ingredients, the selection of an effective, yet safe, reaction temperature, and the extent of mixing and agitation during the reaction.

The formed reaction products, which comprise at least one dihydrocarbyl sulfide, can be separated from the reaction mixture by any suitable separation means such as fractional distillation, or crystallization, or extraction with a suitable solvent (e.g., a liquid paraffin such as n-hexane) plus subsequent evaporation of the solvent. Unreacted process ingredients can be separated in a similar manner and can be recycled to the reaction zone with added fresh ingredients.

The dihydrocarbyl sulfides prepared in accordance with this invention can be used as corrosion inhibitors for metals, solvents, e.g., for heat-resistant polymers such as polysulfones, as lubricant additives, as surfactants, as extractants, e.g., for separating alkanes and alkenes, as intermediates for preparing sulfoxides (different from reactant (a)), which in turn are intermediates in the production of pesticides and pharmaceuticals.

The following examples are presented to further illustrate this invention without unduly limiting the scope of the invention.

EXAMPLE I

This example illustrates the preparation of methyl hexadecenyl sulfide from dimethylsulfoxide (DMSO), and 11-hexadecenyl bromide ($C_{16}H_{31}Br$; prepared by partial hydrogenation of 11-hexadecynyl bromide) in the presence of potassium acetate. 150 mL of DMSO and 30 grams of $C_{16}H_{31}Br$ were mixed with stirring at about 60° C. for about 30 minutes then 20 grams of potassium acetate were added, and the entire mixture was heated with stirring to a temperature of about 130° C., which required a heating time of about 25 minutes. The reaction mixture was maintained at about 127°–135° C. for about 75 minutes.

The cooled reaction mixture was extracted twice with 50 mL of n-hexane. The resulting extract was heated so as to evaporate n-hexane. The desired product, methyl hexadecenyl sulfide, was recovered as high boiling residue. The yield of $CH_3$—S—$C_{16}H_-$ was 96% of the theoretical yield. The product was identified by gas chromotography/mass spectrometry.

EXAMPLE II

In this example a control reaction of dimethyl sulfoxide and 11-hexadecenyl bromide in the presence of potassium carbonate is described. Amounts and reaction conditions were essentially the same as those described in Example I (except unit K$_2$CO$_3$ was employed in lieu of CH$_3$CO$_2$K). Unexpectedly, only a small amount of sulfide was obtained. About 60 weight-% of the product comprised aldehydes and alcohols, and and only 14 weight-% was methyl hexadecenyl sulfide. This result indicates that metal carbonates are not suitable for causing dimethyl sulfoxide and a hydrocarbyl bromide, such as an alkenyl bromide, to react with the formation of primarily methylhydrocarbyl sulfide, such as methyl alkenyl bromide.

Reasonable variations and modifications can be made in this invention without departing from the spirit and scope thereof.

I claim:

1. A process for preparing dihydrocarbyl sulfides comprising the step of simultaneously contacting:
   (a) a dialkyl sulfoxide of the formula

(b) a hydrocarbyl halide of the formula R'-X, and
   (c) a metal carboxylate of the formula

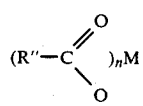

under such conditions as will result in a reaction product comprising at least one alkyl hydrocarbyl sulfide of the formula R-S-R'; wherein the radicals R, which can be the same or different, are alkyl groups containing from 1 to 8 carbon atoms; R' is selected from the group consisting of alkyl groups containing from 1 to 25 carbon atoms, alkenyl groups containing from 3 to 25 carbon atoms and cycloalkyl groups containing from 5 to 25 carbon atoms; X is selected from the group consisting of Cl, Br and I; R" is selected from the group consisting of H and alkyl groups having from 1 to 4 carbon atoms; n is 1 or 2; and M is a mono- or divalent cation of a metal selected from the group of metals belonging to Groups IA, IIA, IVA, IB, IIB VIIB and VIII of the Periodic Table.

2. A process in accordance with claim 1, wherein the metal carboxylate is a Group IA metal carboxylate.

3. A process in accordance with claim 2, wherein R' of the hydrocarbyl halide is selected from the group consisting of alkyl groups and alkenyl groups, each having from 3 to 20 carbon atoms.

4. A process in accordance with claim 2, wherein the dialkyl sulfoxide is dimethyl sulfoxide.

5. A process in accordance with claim 3, wherein the dialkyl sulfoxide is dimethyl sulfoxide.

6. A process in accordance with claim 4, wherein X of the hydrocarbyl halide is Br.

7. A process in accordance with claim 5, wherein X of the hydrocarbyl halide is Br.

8. A process in accordance with claim 3, wherein the dialkyl sulfoxide is dimethyl sulfoxide, the hydrocarbyl halide is a hydrocarbyl bromide, and the metal carboxylate is a Group IA metal acetate.

9. A process in accordance with claim 8, wherein the Group IA metal acetate is potassium acetate and the hydrocarbyl bromide is 11-hexadecenyl bromide.

10. A process in accordance with claim 1, wherein said conditions comprise a reaction temperature ranging from about 50° C. to about 250° C.

11. A process in accordance with claim 9, wherein said conditions comprise a reaction temperature ranging from about 100° C. to about 150° C.

12. A process in accordance with claim 1, wherein said conditions comprise a time of intimate contact of process ingredients (a), (b) and (c) ranging from about 1 minute to about 50 hours.

13. A process in accordance with claim 9, wherein said conditions comprise a time of intimate contact of dimethyl sulfoxide, 11-hexadecenyl bromide and potassium acetate ranging from about 0.2 to about 2 hours.

14. A process in accordance with claim 1, comprising the additional step of separating at least one formed alkyl hydrocarbyl sulfide from the reaction product.

15. A process in accordance with claim 14, wherein said separating step comprises extraction with a liquid paraffin.

16. A process in accordance with claim 1, wherein said contacting is carried out in at least one inert solvent at a temperature in the range of about 50° C. to about 250° C. and wherein said metal carboxylate is a Group IA metal carboxylate.

17. A process in accordance with claim 9, wherein said contacting is carried out at a temperature in the range of about 100° C. to about 150° C. in at least one paraffin, which is liquid at about 25° C. and 1 atm pressure.

18. A process in accordance with claim 17, wherein said paraffin is n-hexane.

19. A process in accordance with claim 1, wherein the mole ratio of (a):(b) ranges from about 1:1 to about 400:1, the mole ratio of (a):(c) ranges from about 2:1 to about 40:1, and the mole ratio of (b):(c) ranges from about 1:10 to about 2:1.

20. A process in accordance with claim 9, wherein the mole ratio of (a):(b) ranges from about 15:1 to about 30:1, the mole ratio of (a):(c) ranges from about 6:1 to about 15:1, and the mole ratio of (b):(c) ranges from about 1:5 to about 1:1.

* * * * *